United States Patent [19]
Dutton

[11] Patent Number: 4,707,132
[45] Date of Patent: Nov. 17, 1987

[54] PROCESS FOR SENSING DEFECTS ON A SMOOTH CYLINDRICAL INTERIOR SURFACE IN TUBING

[76] Inventor: G. Wayne Dutton, 7010 Weld Co. Rd. 1, Longmont, Colo. 80501

[21] Appl. No.: 762,370
[22] Filed: Aug. 5, 1985
[51] Int. Cl.[4] .......................................... G01N 21/47
[52] U.S. Cl. ................................... 356/241; 356/237
[58] Field of Search ................. 356/241, 237; 350/525

[56] References Cited
U.S. PATENT DOCUMENTS 3,981,592  9/1976  Williams .............................. 356/237
4,447,152  5/1984  Rainford et al. .................... 356/237
4,598,997  7/1986  Steigmeier et al. ................. 356/237

FOREIGN PATENT DOCUMENTS 0022851  2/1979  Japan .................................. 356/241
0085308  5/1985  Japan .................................. 356/241

Primary Examiner—Davis L. Willis
Assistant Examiner—S. A. Turner
Attorney, Agent, or Firm—James H. Chafin; Judson R. Hightower

[57] ABSTRACT

The cylindrical interior surface of small diameter metal tubing is optically inspected to determine surface roughness by passing a slightly divergent light beam to illuminate the entire interior surface of the tubing. Impingement of the input light beam components on any rough spots on the interior surface generates forward and backward scattered radiation components. The forward scattered components can be measured by blocking direct and specular radiation components exiting the tubing while allowing the forward scattered radiation to travel past the blocking location. Collecting optics are employed to converge the forward scattered radiation onto a photodetector generating a signal indicative of surface roughness. In the back scattered mode, back scattered radiation exiting the tubing through the entrance opening is reflected 90° by a beam splitter towards collecting optics and a photodetector. Alternatively, back scattered radiation can be transmitted through a fiber optic bundle towards the collecting optics. The input light beam can be supplied through a white light fiber optic bundle mounted coaxial with the first bundle.

12 Claims, 6 Drawing Figures

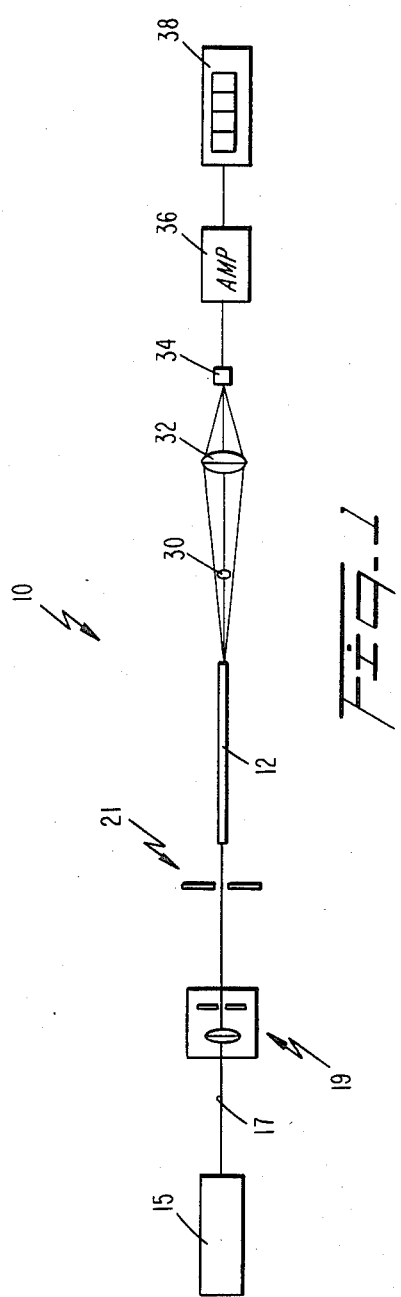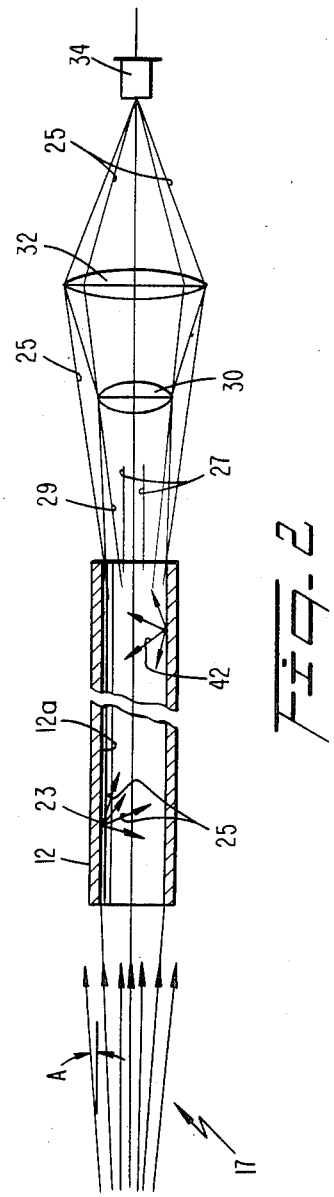

PROCESS FOR SENSING DEFECTS ON A SMOOTH CYLINDRICAL INTERIOR SURFACE IN TUBING

The U.S. Government has rights in this invention pursuant to Contract No. DE-AC04-76DP03533 between the U.S. Department of Energy and Rockwell International.

BACKGROUND OF THE INVENTION

The present invention relates generally to processes for measuring the roughness of a surface and, more particularly, to a process and apparatus for photoelectrically measuring surface roughness of the inside surface of cylindrical tubing.

On machined surfaces requiring a high degree of smoothness such as in mirrors and lenses, semi-conductor wafers, etc., optical detection systems are known for detecting and photoelectrically measuring surface defects or "rough spots". For example, U.S. Pat. 4,030,830 discloses an optical detection system for detecting surface roughness of flat surfaces by converging a laser beam on selected areas of the surface. Back scattered light radiation is measured photoelectrically to provioe an indication of surface roughness. Because the surface is flat, it is possible to tilt it to separate specular reflection from back scattered radiation to produce a back scattered radiation signal using appropriate electronics.

To measure surface roughness of curvilinear surfaces, such as the inside cylindrical surface of metal tubing, different apparatus are employed, such as the device disclosed in U.S. Pat. 4,440,496 to Milana wherein the device is located within the tubing and is translated to analyze the surface by examination of a diffraction pattern generated by laser radiation normal to the surface. Other devices also requiring placement within tubing to examine cylindrical surfaces thereof are disclosed in U.S. Pat. Nos. 3,337,314 and 4,317,632.

Since the aforesaid prior art devices used to detect roughness in tubing must be moved along the inside cylindrical surface, such devices are not practical in examination of metal tubing having small internal diameters (e.g., 1 to 1.5 mm). Also, the aforesaid prior art devices are relatively expensive to manufacture and require expensive equipment supporting their movement within the tubing.

SUMMARY OF THE INVENTION

It is accordingly one object of the present invention to provide a process and apparatus for sensing defects on a smooth cylindrical surface without requiring the apparatus to enter the tubing.

Another object of the invention is to provide a process and apparatus that can be used to sense defects in metal tubing having an inner diameter too small to enable defect sensing apparatus to enter the tubing.

Yet another object of the invention is to provide defect sensing apparatus wherein inner surface roughness of tubing is photoelectrically measured without altering either the tubing or the inner surface finish thereof.

Still another object is to provide a process and apparatus for sensing defects on a smooth inner cylindrical surface of tubing without requiring the apparatus to enter the tubing.

A further object is to provide a defect sensing apparatus that is easy to set up and use and is reliable.

Additional objects, advantages and novel features of the invention will be set forth in detail in part in the description which follows and in part will become apparent to those skilled in the art upon examination of the drawings, or may be learned by practice of the invention. The objects and advantages of the invention may be realized and obtained by means of the instrumentalities and combinations particularly pointed out in the appended claims.

A process for measuring roughness of an inside cylindrical surface of metal tubing, wherein the surface is a high precision smooth surface which may have defects randomly distributed thereon, comprises the steps of producing a light beam having a diameter at least equal to the inner diameter of the tubing and directing the beam so that it enters and travels through the tubing to impinge on the defects, causing generation of surface scattered light components. These sufface scattered components are collected at a location outside of the tubing and are used to generate and display a scattered light component signal providing information on the surface roughness.

According to one embodiment of the invention, a laser beam passing through a spatial filter and iris enters the tubing longitudinally and diverges slightly. The diameter of the beam is adjusted to completely illuminate the cylindrical surface along the entire length of the tubing. As the diverging wavefront of the laser beam travels through the tubing, the incident light beam reflecting off the cylindrical surface strikes any "rough spots" randomly formed on the cylindrical surface, scattering components of the incident light beam. Forward scattered components together with direct light beam components and specular reflection components exit the tubing.

Since the travel vectors of the direct and specular reflection components are known, a zero order stop can be positioned along the longitudinal axis of the tubing to block further passage of these components. Forward scattered radiation travels past the stop where the radiation is focused with a collecting lens onto a photodetector.

In accordance with a second embodiment or the invention, surface roughness may be detected by measuring back scattered radiation. The laser beam passes through an iris and beam splitter into the tubing along its axis. The back scattered radiation exits the tubing through the entrance opening, striking the beam splitter tilted at about a 45° angle to the longitudinal axis. The back scattered radiation is reflected 90° by the beam splitter where it is converged by a lens.

Measurement of back scattered radiation in the aforesaid manner provides a more reliable signal indicat:ve of surface roughness than the forward scattering method. The back scattering method is easier to set up since it does not require coaxial alignment of the converging lens and photodetector with the longitudinal axis of the tubing and laser as in the forward scattering method. In addition, the back scattering method may be employed for tubing open at only one end, or at both ends.

The back scattering method is easiest to employ when utilizing fiber optics. In a third embodiment of the invention, a fiber optic bundle connected to a source of white light enters a tubular carrier through a microborescope housing. The carrier extends between the microborescope housing and small diameter tubing along the longitudinal axis thereof to transmit a white light beam from the fibers to illuminate the cylindrical surface. Back scattered radiation is transmitted from the tubing through a bundle of graduated index imaging ribers formed coaxially outside the white light fiber bundle. The imaging fiber bundle extends through the tubular carrier and the microborescope housing to transmit light to a collecting lens where it is converged onto a pnotodetector.

BRIEF DESCRIPTION OF THE DRAWING

FIG. 1 is a schematic view of a first embodiment of the invention for determining inner surface roughness of tubing by detection of forward scattered radiation;

FIG. 2 is an enlarged, partial sectional view of the system of FIG. 1;

DETAILED DESCRIPTION OF THE INVENION

Figure 3:
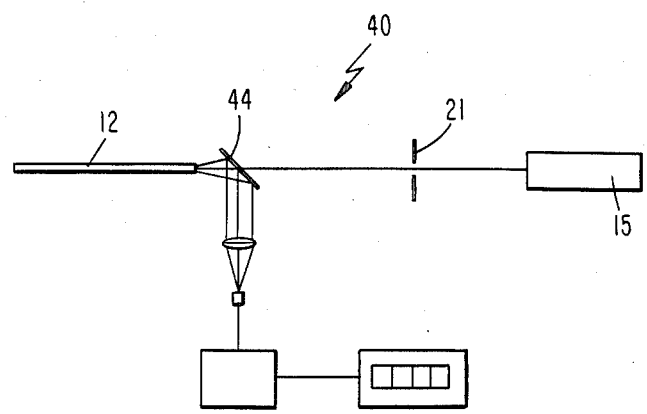
FIG. 3 is a schematic view of a second embodiment of the invention for measuring back scattered radiation.

FIGS. 1 and 2 are illustrations of a system 10 in accordance with the present invention, used for determining the inner surface roughness at 12a of cylindrical metal tubing 12. The tubing 12 is held magnetically within a V block holder (not shown) mounted on a leveling table. A laser 15, such as a 5 millivolt He-Ne, He-Cd or Argon laser, in coaxial alignment with tubing 12, generates a laser beam 17 entering the tubing at a slightly divergent angle A after passing through a spatial filter 19 and iris 21. The diameter of laser beam 17 is slightly greater than the internal diameter of tubing 12 to completely illuminate surface 12a along the entire length of the tubing.

As the diverging wavefront of laser beam 17 travels through tubing 12, the incident light beam reflecting off surface 12a strikes any "rough spots" 23, randomly formed on the cylindrical surface. These rough spots 23 alter the direction of travel of components the incident light beam. The altered light beam components, together with direct radiation components 27 that travel through tubing 12 without contacting surface 12a and with specular reflection components 29, exit tubing 12 as forward scattered light components.

Since the travel vectors of direct radiation components 27 and specular reflection components 29 are known, a zero order stop 30 can be positioned along the longitudinal axis of and downstream from tubing 12 to block passage of these components. By appropriate selection of the diameter of stop 30, forward scattered radiation components 25 travel past the zero order stop where they are focused with a collecting lens 32 onto a photodetector 34 which may, for example, be a PMT or a photodiode. A signal generated by detector 34 and amplified by amplifier 36, may appear as a voltage readout on a millivolt meter 38. Assuming proper calibration, the signal representative of forward scattered radiation provides an indication of surface roughness.

In a working embodiment of system 10, laser 15 is a 5 millivolt He-Ne laser, such as Model 120 manufactured by Spectra-Physics, Mountain View, Calif. Spatial filter 19 such as Model 900 (25 micrometer pin hole and 10× objective lens, focal length of 5 millimeters) manufactured by Newport Research Corporation, Fountain Valley, Calif., is employed with an iris having a diameter of 3 millimeters (e.g., Model ID-1.5 also manufactured by Newport Research Corporation) to transmit the light beam into tubing 12 having an internal diameter of approximately 1 to 2 millimeters. The zero order stop 30 has a diameter of about 3 millimeters and is employed in conjunction with a converging lens 32 having a diameter of about 50 millimeters and a focal length of about 140 millimeters. Photodetector 34 is conventional, such as Model SGD-040 Photodiode from EG&G, Electronic Products Division, Boston, Mass.

Figure 4:
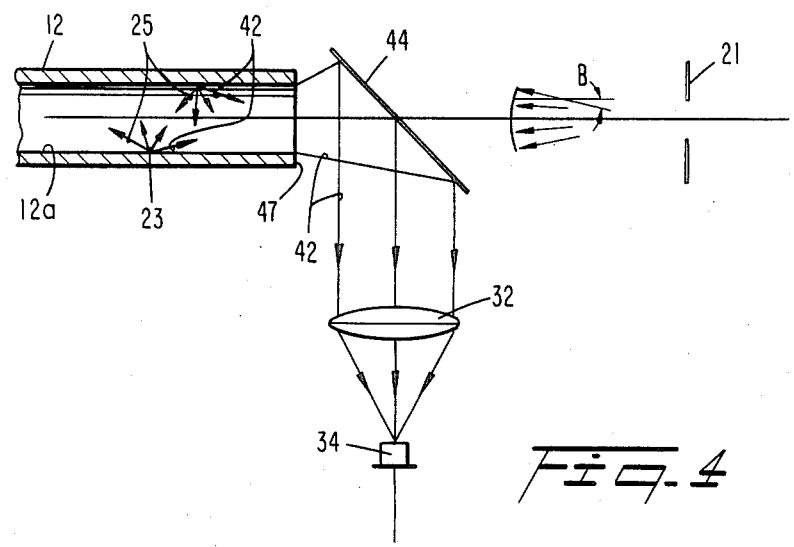
FIG. 4 is an enlarged, partial sectional view of the system of FIG. 3.

FIGS. 3 and 4 are illustrations of a second embodiment of the invention, wherein a system 40 is used to measure roughness of cylindrical surface 12a by measurement of back scattered radiation 42 (see FIG. 4). In system 40, laser 15 is in coaxial alignment with tubing 12 to generate laser beam 17 entering the tubing at a slightly divergent angle B after passing through iris 21 and a pellicle beam splitter 44 (e.g. Model 2289401 available from Ealing Corporation, Cambridge, Mass.) situated along the longitudinal axis of the tubing. With reference to FIG. 4, beam 17 enters the tubing to illuminate the entire interior surface thereof. Impact of the incident light beam reflecting off surface 12a against any rough spots 23 result in generation of back scattered radiation components 42.

Back scattered radiation 42 exits tubing 12 from the entrance opening where it is deflected at 90° by means 44. Back scattered radiation 42 is then converged by lens 32 onto photodetector 34 to generate a signal indicative of surface roughness in the manner described above.

Based upon extensive experimentation, it has been observed that system 40 provides a better indication or surface roughness than system 10. In part, this is due to the difficulty in both obtaining and maintaining precise alignment of the component parts in system 10 along the longitudinal axis of small diameter tubing 12 (e.g., 1 to 2 millimeters in diameter). By employing beam splitter 44 in system 40, a slight deviation in alignment of the beam splitter with the longitudinal axis will not affect signal reliability since the beam splitter has a sufficient surface area to reflect an appreciable back scattered radiation component 42 even if mis-alignment occurs. Of course, with system 40, there is no need to align the collecting lens 32 and photodetector 34 with the small diameter tubing.

Whereas system 10 can be employed only in connection with small diameter tubing 12 open at opposite ends thereof, system 40 can be employed with tubing open at both opposite ends or at only one end 47 (facing the beam splitter).

Figure 5:
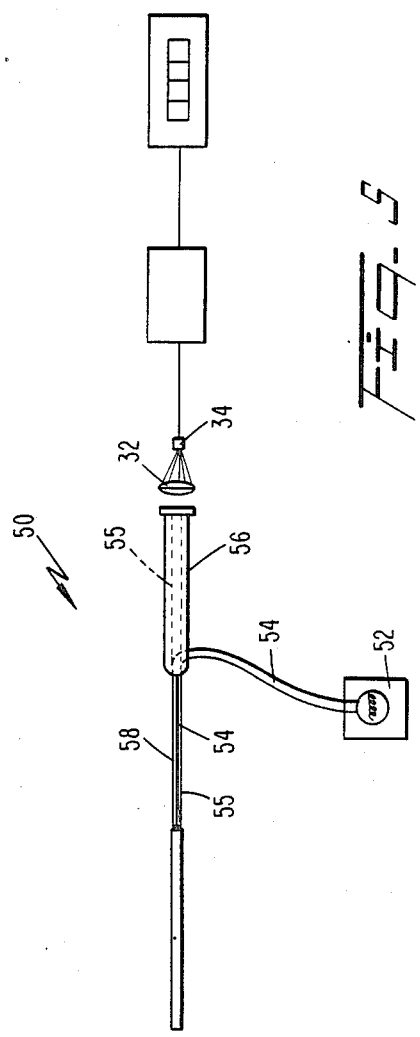
FIG. 5 is a schematic view of a third embodiment of the present invention employing fiber optics for measurement of back scattered radiation.
Figure 6:
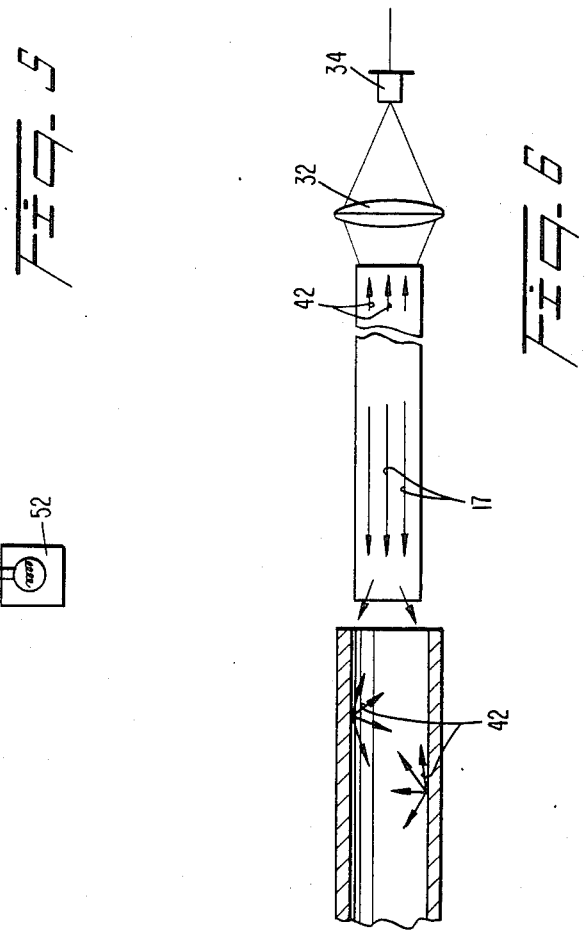
FIG. 6 is an enlarged plan view of the system of FIG. 5.

FIGS. 5 and 6 are illustrations of a third embodiment of the invention wherein a system 50 employs fiber optics for generating an incident incoming light beam 17 and transmitting back scattered radiation components toward converging lens 32. More specifically, system 50 comprises a white light source 52 producing white light transmitted through a fiber optic bundle 54 into a borescope housing 56 in coaxial alignment with tubing 12. The borescope housing 56, such as a Dyonics Microborescope with Model 375A light source, available from Dyonics Inc., Hanover, Mass., includes appropriate connections (not shown in detail) through which bundle 54 enters the housing to extend in coaxial alignment towards the entrance opening of tubing 12 through a non-flexible tubular carrier 58. The carrier 58 is secured to one end of housing 56 and extends in coaxial alignment with tubing 12, terminating approximately 1 to 2 millimeters from the entrance opening to transmit a slightly divergent white light beam from the fibers to illuminate the interior cylindrical surface 12a.

Back scattered radiation 42 is directed towards the converging lens 32 by a graduated imaging fiber optic bundle 55 extending through the tubular carrier 58 and housing 56. Preferably, the imaging fiber optic bundle 55 coaxially surrounds the white light bundle 54 within the carrier; however, it will be understood that the graduated index imaging fibers may be interspersed between the white light fibers. The internal diameter of the carrier is slightly greater than the internal diameter of tubing 12 and preferably is spaced not more than 2 millimeters from the entrance opening of the tubing to avoid reflection of light against the tubing end wall.

As a result of extensive experimentation, system 50 provides a more reliable indication or surface roughness in comparison with systems 10 and 40 discussed supra.

In the forward scattering system 10, the angle of divergence A of the incoming light beam 17 is approximately 15 to 35 milliradians and preferably 25 milliradians. In back scattering system 40, angle of divergence B is in the approximate range of 3 to 7 milliradians and preferably 5 milliradians. In fiber optic system-50, the white light beam divergence angle is in the approximate range of 25 to 55 milliradians and preferably 40 milliradians.

Each of the aforesaid systems and methods according to the present invention provides a means for measuring surface finish within the interior of small diameter metal tubing which is inaccessible to conventional stylus-type or optical surface analyzers. Surface measurement is accomplished without contacting the surface and without altering either the tubing or its surface finish. If surface roughness of a tested specimen of tubing 12 is unsatisfactory, the interior cylindrical surface finish can be smoothened by passivation with a suitable acid for etching the interior surface. Tubing specimen 12 can then be re-tested with one of systems 10, 40 or 50 until a desired degree of smoothness is obtained, resulting in fewer rejects.

The foregoing description of preferred embodiments of the invention have been presented for purposes of illustration and description. It is not intended to be exhaustive or to limit the invention to the precise form disclosed. Obvious modifications or variations are possible in light of the above teachings. The embodiments were chosen and described in order to best illustrate the principles or the invention and its practical application to thereby enable one of ordinary skill in the art to best utilize the invention and various embodiments and with various modifications as are suited to the particular use contemplated. It is intended that the scope of the invention be defined by the claims appended hereto.

What is claimed is:

1. A process for measuring roughness of an inside cylindrical surface of metal tubing, wherein said surface is a high-precision smooth surface which may have defects randomly distributed thereon, comprising the steps of:
    (a) producing a light beam having a diameter at least equal to the inner diameter of said tubing;
    (b) directing said beam so that it enters and travels through the tubing where it impinges on defects on said cylindrical surface, causing generation of surface scattered light components;
    (c) collecting only said surface scattered light components at a location outside said tubing; and
    (d) generating and displaying a scattered light component signal providing information as to the surface roughness of said surface.

2. A process according to claim 1, including the step of producing said light beam so that it is slightly divergent as it enters the tubing.

3. The process of claim 2, wherein said light beam is a laser beam, and including the step of filtering said beam before it passes into the tubing to reduce spatial noise.

4. The process of claim 3, wherein said tubing is open at both ends thereof and including the further step of blocking direct and specular reflection light components exiting from the tubing while allowing the surface scattered light components to by-pass the blocking location.

5. The process of claim 4, including the step of converging said scattered light components towards a photo-detecting unit for generating said scattered light radiation signal.

6. The process of claim 4, wherein said scattered light collected is forward scattered light.

7. The process of claim 1 wherein said scattered light is back scattered light, and including the further step of directing said back scattered light exiting from the tubing in a direction generally perpendicular to the path of the incoming light beam.

8. The process of claim 7, wherein said back scattered light is reflected to travel in a direction perpendicular to the direction of incoming light with a beam splitter positioned along the longitudinal axis of the incoming light path, thereby permitting said incoming light beam to pass through the beam splitter into the tubing.

9. The process of claim 1, wherein said light beam is produced by means of a white light source offset with respect to the longitudinal axis of said tubing to transmit the light beam entering the tubing along the longitudinal axis by means of a fiber-optic cable.

10. The process of claim 9, comprising the further step of directing back scattered light components exiting from the tubing towards a collecting location located on said longitudinal axis.

11. A process for measuring roughness of an inside cylindrical surface of small diameter tubing, wherein said surface is a high precision smooth surface which may have defects randomly distributed thereon, comprising the steps of:
    (a) producing a filtered, slightly divergent laser beam having a diameter at least equal to the inner diameter of said tubing;
    (b) directing said beam so that it enters and travels through the tubing generally along the longitudinal axis thereof, and exits from the tubing with a direct beam component, a specularly reflected light component, and surface scattered light component;
    (c) blocking direct and specular reflection light components exiting from the tubing while the allowing the scattered light beam components to by-pass the blocking location;
    (d) collecting the scattered light components at a predetermined distance from the blocking location; and
    (e) generating and displaying a scattered light radiation signal providing information as to the surface roughness.

12. A process for measuring roughness of an inside cylindrical surface of small diameter tubing, wherein said surface is a high precision smooth surface which may have defects randomly distributed thereon, comprising the steps of:
 (a) producing a slightly divergent laser beam having a diameter at least equal to the inner diameter of said tubing;
 (b) directing said beam so that it enters and travels through the tubing generally along the longitudinal axis thereof, while impinging on defects formed on said inside surface causing generation of back scattered light radiation;
 (c) directing said back scattered light exiting from the tubing in a direction different from the direction of said incoming light beam;
 (d) collecting the back scattered light components at a location offset with respect to the longitudinal axis of said tubing; and
 (e) generating and displaying a back scattered light radiation signal providing information as to the surface roughness.

* * * * *